United States Patent
Schmitt

(10) Patent No.: US 6,394,353 B1
(45) Date of Patent: *May 28, 2002

(54) MEDICAL DEVICE WITH CONTROL ARANGEMENT FOR A DEVICE COMPONENT

(75) Inventor: Thomas Schmitt, Forchheim (DE)

(73) Assignee: Siemens Aktiengesellschaft, Munich (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/078,609

(22) Filed: May 14, 1998

(30) Foreign Application Priority Data

Jun. 5, 1997 (DE) .......................... 197 23 627

(51) Int. Cl.⁷ .................. G06F 17/00; G06F 19/00; G06K 7/10
(52) U.S. Cl. ..................... 235/462.15; 235/462.13; 378/162
(58) Field of Search ................ 235/435, 440, 235/444, 453, 441, 462.01, 449, 462.15, 462.13; 378/162, 165, 174, 182, 207

(56) References Cited

U.S. PATENT DOCUMENTS

| | | | |
|---|---|---|---|
| 3,402,650 A | | 9/1968 | Hoadley |
| 3,601,024 A | | 8/1971 | Pagel |
| 3,911,397 A | * | 10/1975 | Freny, Jr. .................... 340/147 |
| 3,987,277 A | * | 10/1976 | Kratt et al. .......... 235/61.11 C |
| 4,684,791 A | * | 8/1987 | Bito ............................ 235/380 |
| 4,791,282 A | * | 12/1988 | Schmidt et al. ............. 235/462 |
| 5,404,871 A | * | 4/1995 | Goodman et al. ...... 128/200.14 |
| 5,428,214 A | * | 6/1995 | Hakkers et al. ............. 235/492 |
| 5,640,002 A | * | 6/1997 | Ruppert et al. ............. 235/472 |
| 5,640,004 A | * | 6/1997 | Mardinian et al. .......... 235/492 |
| 5,679,945 A | * | 10/1997 | Renner et al. .............. 235/492 |
| 5,825,002 A | * | 10/1998 | Roslak ........................ 235/375 |
| 5,905,249 A | * | 5/1999 | Reddersen et al. .... 235/462.15 |

FOREIGN PATENT DOCUMENTS

| | | |
|---|---|---|
| DE | 31 47 956 | 1/1984 |
| DE | 36 09 527 | 5/1987 |
| GB | 2 110 564 | 6/1983 |

* cited by examiner

Primary Examiner—Karl D. Frech
(74) Attorney, Agent, or Firm—Schiff Hardin & Waite

(57) ABSTRACT

In a medical device with a control arrangement for at least one device component, a code reader is employed to the control arrangement for reading a component-specific code allocated to the (at least one) device component. A configuration or reconfiguration of the control arrangement ensues on the basis of this code, when necessary. It is thus possible to exchange and/or to expand device components in a simple fashion without having to exchange the control arrangement or modify it in an expensive manner.

4 Claims, 3 Drawing Sheets

MEDICAL DEVICE WITH CONTROL ARANGEMENT FOR A DEVICE COMPONENT

BACKGROUND OF THE INVENTION

1. Field of the Invention

The present invention is directed to a medical device having at least one device component with a control arrangement for controlling the device component.

2. Description of the Prior Art

Medical devices typically include a number of device components which can be for example, a mounting plate, a radiation receiver, a radiation transmitter, a radiation diaphragm, an operating unit, etc. A control arrangement is further provided which operates one or more of these components for conducting a medical examination or treatment of an examination subject. To this end, the device components are connected mechanically and/or electrically with the control arrangement and possibly with each other. Particularly in complex medical devices, such a control arrangement frequently employs a computer which receives and evaluates signals from the components and/or transmits signals thereto. By means of a specific control program, the control signals required by each device component are forwarded to the device component, or the signal emanating from a device component is evaluated in the desired manner. Thus the control arrangement is provided in the medical device with connections to its device components. Should the medical device subsequently be reconfigured with a new or another device component, then the control arrangement must be correspondingly modified, which can ensue through a modification of the control parameters of the controlling sequence, of the control program, and/or by completely exchanging of the "old" control arrangement with a modified control arrangement. This kind of exchange of a device components usually very expensive, sometimes positively so.

SUMMARY OF THE INVENTION

An object of the present invention to provide a way of reconfiguring a medical device of the aforementioned type such that an exchange and/or a modification of a device component is possible and less costly.

The above object is achieved in accordance with the principles of the present invention in a medical device wherein the control arrangement includes a code reader allocated to at least one device component controlled by the control arrangement, the code reader reading a component-specific code allocated to the device component. If and when a reconfiguration of the control arrangement becomes necessary, the reconfiguration can be undertaken on the basis of the code read by the code reader.

By providing a means for reading a component-specific code allocated to the device component, a device-specific configuration of the control arrangement can ensue in a simple and cost-effective manner. An exchange or a modification of a device component is thus possible, costs less, and is less cost-intensive relative to conventional procedures.

DESCRIPTION OF THE PREFERRED EMBODIMENTS

Figure 1:
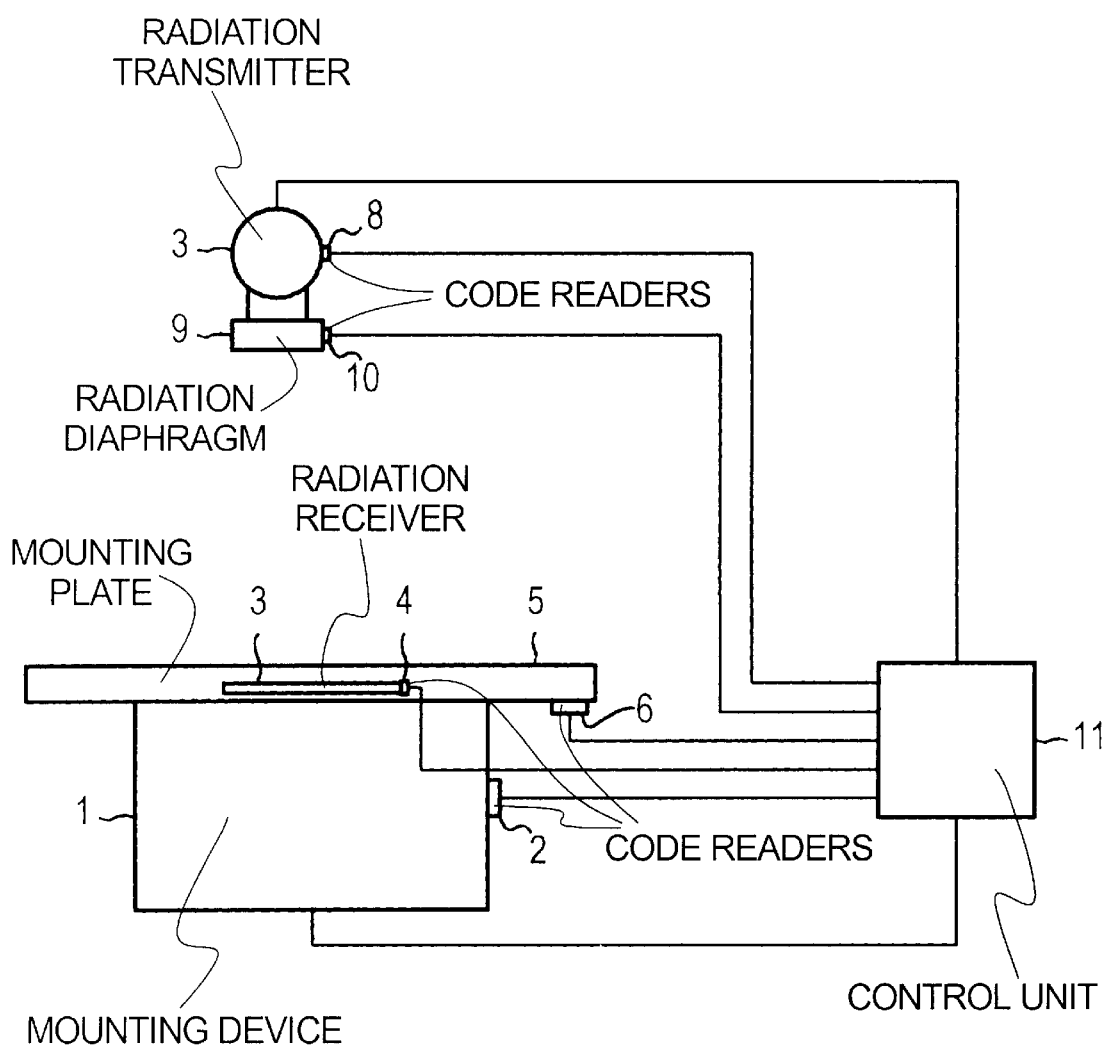
FIG. 1 is a schematic block diagram of a medical device according to the invention.
Figure 6:
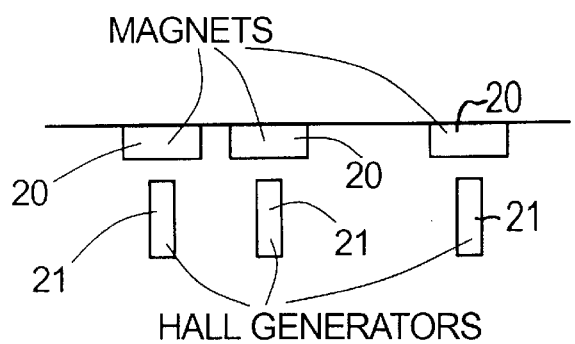
FIG. 6 illustrates a device for reading a magnetic code in accordance with the invention.
Figure 7:
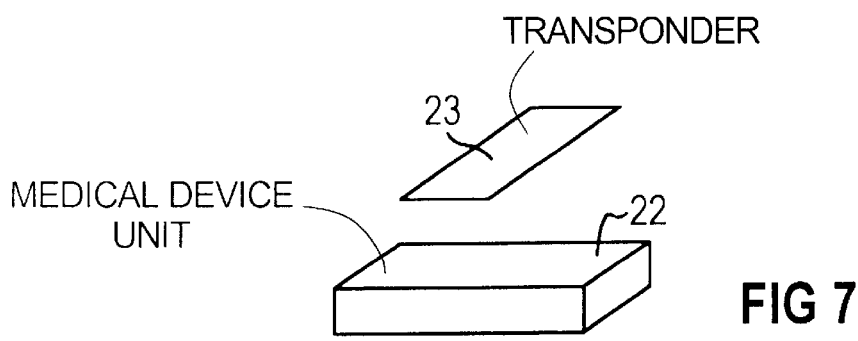
FIG. 7 illustrates a device component with a device transporter in accordance with the invention.

In the medical device depicted in a basic fashion in FIG. 1, each device component has a code reader connected thereto for reading a component-specific code allocated to the device component. For example, a code reader 2 is allocated to a mounting device 1; a code reader 4 is allocated to a radiation receiver 3; a code reader 6 is allocated to a mounting plate 5; a code reader 8 is allocated to a radiation transmitter 7; a code reader 10 is allocated to a radiation diaphragm (gate) 9. The signals of the code readers 2, 4, 6, 8 and 10 are fed to a control unit 11 which transmits corresponding control signals to, or receives status or parameter signals from one or more of the device components 1, 3, 5, 7, 9 for operation of the medical device with respect to the treatment and/or diagnosis of an examination subject. On the basis of the code specific to each component 1, 3, 5, 7, 9, a configuration of the control unit 11 ensues, e.g. with respect to the modification of its control program, which is especially advantageous if a device component is exchanged, modified, and/or expanded. The code readers 2, 4, 6, 8, 10 can be configured to read any of a mechanical, electrical, electro-optical, acoustical and/or magnetic code, as depicted in FIGS. 2 to 6. It is particularly advantageous to utilize device transponders allocated to the respective device components 1, 3, 5, 7, 9, as depicted in FIG. 7, for example.

Figure 2:
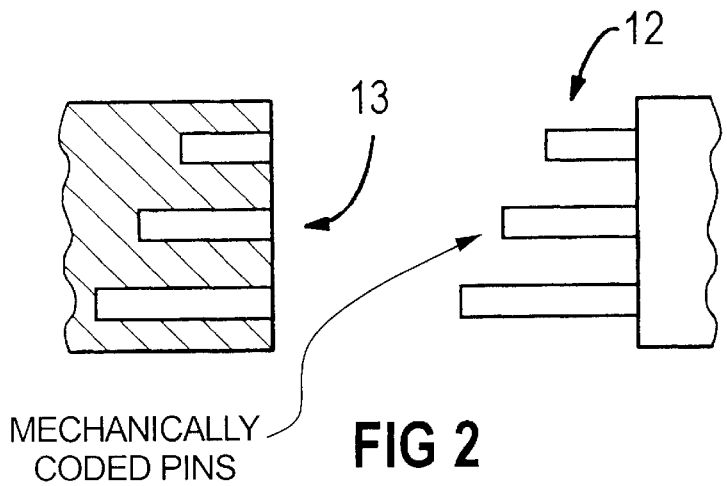
FIG. 2 illustrates a device for reading a mechanical code in accordance with the invention.

FIG. 2 depicts in basic fashion a device for reading a mechanical code, wherein coded pins 12 arranged at a part of the medical device can engage in recesses 13 arranged at another part of the medical device.

Figure 3:
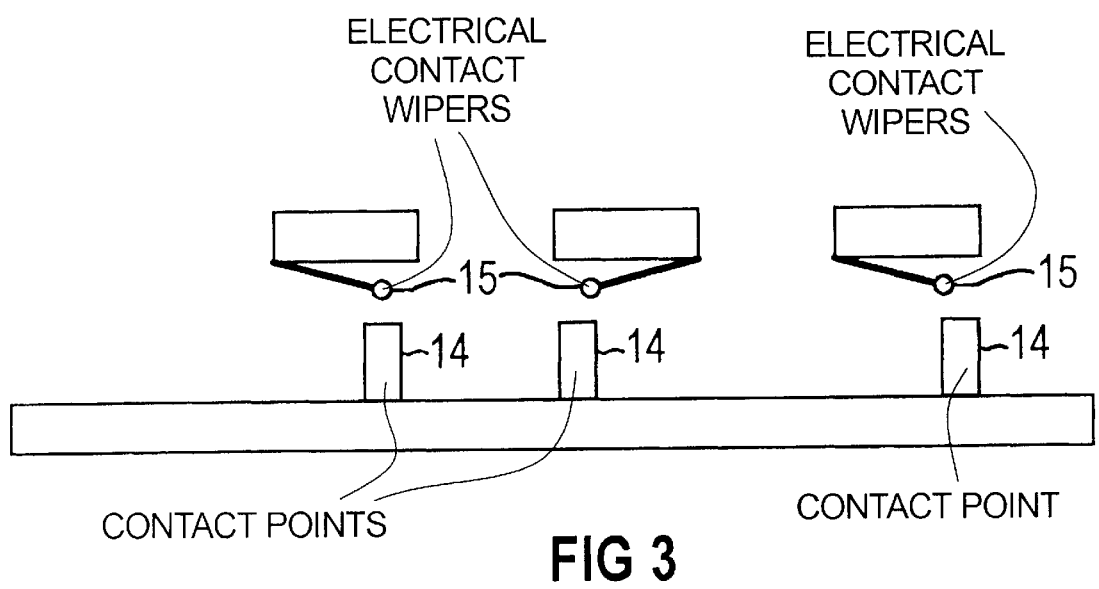
FIG. 3 illustrates a device for reading an electrical code in accordance with the invention.

An arrangement for reading an electrical code is depicted in FIG. 3, for example. Contact points 14 arranged at one part of the medical device are supplied with different voltages and are interrogated as codings by contact wipers 15 arranged at another part of the medical device, for example.

Figure 4:
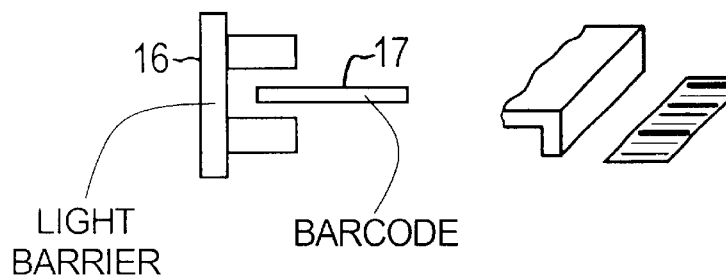
FIG. 4 illustrates a device for reading an electro-optical code in accordance with the invention.

FIG. 4 shows an arrangement for reading an electro-optical code, in which a light barrier 16 can be used which is arranged at one part of the medical device and is designed for reading a bar code 17 arranged at another part of the medical device.

Figure 5:
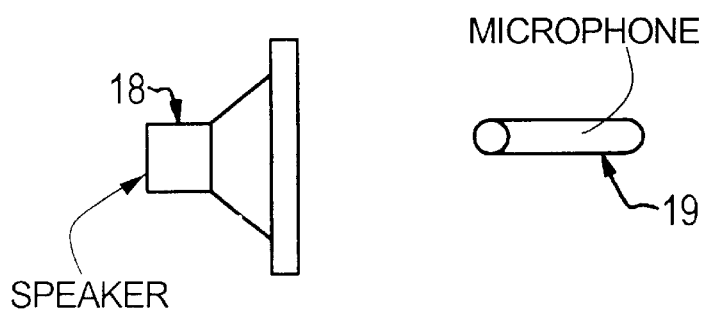
FIG. 5 illustrates a device for reading an acoustical code in accordance with the invention.

The coding can also ensue acoustically, as depicted in FIG. 5, using a speaker 18 for transmitting acoustical signals, arranged at one part of the medical device, and a microphone 19 for receiving the acoustical signals arranged at another part of the medical device.

The acoustical signals are generated and evaluated in any known manner and thus acoustical signal generating and evaluating units are explicitly depicted.

Using magnets 20 and Hall generators 21, coding can likewise ensue by varying the power of the magnetic field emanating from the magnets 20. Such an exemplary embodiment is depicted in FIG. 6. The magnets 20 are arranged at one part of the medical device, and the Hall generator 21 at another part.

As depicted in FIG. 7, a part of the medical device exemplified the unit 22 can be configured for activating and reading out a transponder 23 arranged at another part of the medical device, by means of which a coding can likewise ensue.

Within the context of the invention, the medical device can be configured for treatment or diagnosis of an examination subject by means of physical properties. The application of the invention is especially advantageous in an X-ray diagnostic or therapeutic device, particularly in an X-ray device, in a magnetic resonance device, in a device working with acoustical waves, or with a device working with magnetic or electrical properties.

Although various minor modifications might be suggested by those skilled in the art, it should be understood that I wish to embody within the scope of the patent warranted hereon all such modifications as reasonably and properly come with the scope of my contribution to the art.

I claim as my invention:

1. A medical device comprising:

a configurable control unit;

a plurality of medical device components collectively operable to perform a medical diagnostic procedure, including at least one medical device component which dictates a configuration of said configurable control unit;

said configurable control unit being connected to said medical device components to control said medical diagnostic procedure, said configurable control unit controlling said medical procedure differently dependent on a presence of said at least one medical device component; and a code reader in communication with said at least one medical device component and with said control unit, for reading a component-specific code uniquely allocated to said at least one medical device component which identifies said at least one medical device component, and which supplies said code to said control unit, said control unit, upon receipt of said code, being reconfigured to control said medical diagnostic procedure differently dependent on said presence of said at least one medical device component.

2. A medical device as claimed in claim 1 wherein said code reader comprises a code reader for reading a code selected from the group consisting of a mechanical code, an electrical code, an electro-optical code, an acoustical code, and a magnetic code.

3. A medical device as claimed in claim 1 further comprising a device-specific transponder allocated to said device component, and wherein said code reader comprises means for interrogating said device-specific transponder.

4. A medical device as claimed in claim 1 wherein said plurality of medical device components are collectively operable to perform a radiological examination, as said medical diagnostic procedure.

* * * * *